US008823933B2

(12) United States Patent
Bonciolini et al.

(10) Patent No.: US 8,823,933 B2
(45) Date of Patent: Sep. 2, 2014

(54) SUBSTRATE-LIKE PARTICLE SENSOR

(75) Inventors: Dennis J. Bonciolini, Tigard, OR (US);
Craig C. Ramsey, West Linn, OR (US);
DelRae H. Gardner, Tualatin, OR (US);
Felix J. Schuda, Saratoga, CA (US)

(73) Assignee: CyberOptics Corporation, Golden Valley, MN (US)

( * ) Notice: Subject to any disclaimer, the term of this patent is extended or adjusted under 35 U.S.C. 154(b) by 211 days.

(21) Appl. No.: 11/904,633

(22) Filed: Sep. 27, 2007

(65) Prior Publication Data

US 2008/0239314 A1    Oct. 2, 2008

Related U.S. Application Data

(60) Provisional application No. 60/848,336, filed on Sep. 29, 2006.

(51) Int. Cl.
*G01N 21/00*    (2006.01)

(52) U.S. Cl.
USPC .......................................... 356/338

(58) Field of Classification Search
USPC .......................................... 356/338
See application file for complete search history.

(56) References Cited

U.S. PATENT DOCUMENTS

| | | | |
|---|---|---|---|
| 1,668,328 A | 5/1928 | Martien | |
| 3,815,020 A | 6/1974 | Mayer | |
| 3,835,264 A | 9/1974 | Overby | |
| 3,861,981 A | 1/1975 | Loo | 156/345.18 |
| 3,876,833 A | 4/1975 | Broers et al | 250/492 |
| 3,876,883 A | 4/1975 | Broers et al. | 250/492 |
| 4,033,053 A | 7/1977 | Engler | |
| 4,074,114 A | 2/1978 | Dobras | 235/462.07 |
| 4,119,381 A | 10/1978 | Muka et al. | 356/244 |
| 4,180,199 A | 12/1979 | O'Rourke et al. | 228/102 |
| 4,260,258 A | 4/1981 | Rose et al. | 356/335 |
| 4,528,451 A | 7/1985 | Petric et al. | 250/441.1 |
| 4,633,578 A | 1/1987 | Aine et al. | |
| 4,659,220 A * | 4/1987 | Bronte et al. | 356/237.5 |
| 4,701,096 A | 10/1987 | Fisher, Jr. | 414/416.08 |
| 4,746,215 A | 5/1988 | Gross | 356/339 |
| 4,753,569 A | 6/1988 | Pryor | 414/730 |
| 4,791,482 A | 12/1988 | Barry et al. | 348/136 |
| 4,810,996 A | 3/1989 | Glen et al. | |

(Continued)

FOREIGN PATENT DOCUMENTS

| | | |
|---|---|---|
| CA | 1239785 | 8/1988 |
| DE | 19633032 | 2/1997 |

(Continued)

OTHER PUBLICATIONS

Search report of European Patent Office in Patent Application PCT/US2007/020814 filed Sep. 27, 2007.

(Continued)

*Primary Examiner* — Roy M Punnoose
(74) *Attorney, Agent, or Firm* — Christopher R. Christenson; Kelly, Holt & Christenson, PLLC

(57) ABSTRACT

A substrate-like particle sensor includes a substrate-like base portion and an electronics enclosure disposed on the substrate-like base portion. A power source is located within the electronics enclosure. A controller is operably coupled to the power source. A particle sensor is operably coupled to the controller and provides an indication to the controller of at least one particle present near the particle sensor.

10 Claims, 6 Drawing Sheets

(56) References Cited

U.S. PATENT DOCUMENTS

| | | | |
|---|---|---|---|
| 4,843,287 A | 6/1989 | Taft | 318/568.16 |
| 4,880,384 A | 11/1989 | Murphy | |
| 4,891,030 A | 1/1990 | Gertzfeld | |
| 4,918,627 A | 4/1990 | Garcia et al. | 702/82 |
| 4,984,889 A | 1/1991 | Sommer | 356/336 |
| 4,985,601 A | 1/1991 | Hagner | 174/261 |
| 5,011,286 A | 4/1991 | Petralli | 356/343 |
| 5,033,851 A | 7/1991 | Sommer | 356/338 |
| 5,055,637 A | 10/1991 | Hagner | 174/260 |
| 5,061,065 A | 10/1991 | Sommer | 356/246 |
| 5,076,794 A | 12/1991 | Ganthier | |
| 5,092,675 A | 3/1992 | Sommer | 356/338 |
| 5,175,601 A | 12/1992 | Fitts | 356/604 |
| 5,232,331 A | 8/1993 | Kasai et al. | 414/802 |
| 5,248,553 A | 9/1993 | Miyashita et al. | |
| 5,265,957 A | 11/1993 | Moslehi et al. | 374/1 |
| 5,267,143 A | 11/1993 | Pryor | 700/56 |
| 5,276,609 A | 1/1994 | Durlach | |
| D344,302 S | 2/1994 | Plagborg | |
| 5,298,363 A | 3/1994 | Weiss | 430/296 |
| 5,301,248 A | 4/1994 | Takanori et al. | 382/147 |
| 5,321,989 A | 6/1994 | Zimmer et al. | 73/724 |
| 5,371,585 A | 12/1994 | Morgan et al. | 356/246 |
| 5,371,728 A | 12/1994 | Sakai et al. | |
| 5,382,911 A | 1/1995 | Cotler et al. | |
| 5,393,706 A | 2/1995 | Mignardi et al. | |
| 5,435,682 A | 7/1995 | Crabb et al. | 414/217 |
| 5,442,297 A | 8/1995 | Verkuil | |
| 5,444,637 A | 8/1995 | Smesny et al. | 364/556 |
| 5,521,123 A | 5/1996 | Komatsu et al. | 437/209 |
| 5,565,984 A | 10/1996 | Girvin | 356/336 |
| 5,573,728 A | 11/1996 | Loesch et al. | 422/90 |
| 5,576,831 A * | 11/1996 | Nikoonahad et al. | 356/623 |
| 5,581,523 A | 12/1996 | Seki et al. | 369/44.11 |
| 5,619,027 A | 4/1997 | Ackley | 235/462.01 |
| 5,641,911 A | 6/1997 | Ryhanen | 73/718 |
| 5,642,293 A | 6/1997 | Manthey et al. | 702/42 |
| 5,675,396 A | 10/1997 | Tsunehiro | 349/59 |
| 5,680,384 A | 10/1997 | Seki et al. | |
| 5,721,677 A | 2/1998 | Pryor | 700/61 |
| 5,726,066 A | 3/1998 | Choi | 437/3 |
| 5,742,702 A | 4/1998 | Oki | 382/156 |
| 5,783,341 A | 7/1998 | Uzawa | 430/22 |
| 5,784,282 A | 7/1998 | Abitbol et al. | 700/186 |
| 5,786,704 A | 7/1998 | Kim | 324/765 |
| 5,805,289 A | 9/1998 | Corby et al. | 356/614 |
| 5,839,215 A | 11/1998 | Lasprogata | |
| 5,854,880 A | 12/1998 | Pryor | 700/259 |
| 5,864,399 A | 1/1999 | Girvin et al. | 356/339 |
| 5,946,093 A | 8/1999 | DeFreez et al. | 356/339 |
| 5,956,417 A | 9/1999 | Pryor | 382/154 |
| 5,962,909 A | 10/1999 | Jerominek et al. | 257/522 |
| 5,969,639 A | 10/1999 | Lauf et al. | 340/870.17 |
| 5,973,788 A | 10/1999 | Petersen et al. | 356/614 |
| 5,981,116 A | 11/1999 | Ota | 430/22 |
| 6,010,009 A | 1/2000 | Peterson et al. | 206/711 |
| 6,011,294 A | 1/2000 | Wetzel | |
| 6,013,236 A | 1/2000 | Takahashi et al. | 423/345 |
| 6,022,811 A | 2/2000 | Yuuki et al. | 438/758 |
| 6,075,909 A * | 6/2000 | Ressl | 385/14 |
| 6,106,457 A | 8/2000 | Perkins et al. | 600/175 |
| 6,111,642 A | 8/2000 | DeFreez et al. | 356/337 |
| 6,129,278 A | 10/2000 | Wang et al. | 235/462.01 |
| 6,137,572 A | 10/2000 | DeFreez et al. | 356/339 |
| 6,175,124 B1 | 1/2001 | Cole et al. | 257/48 |
| 6,184,773 B1 | 2/2001 | Bonne et al. | |
| 6,206,441 B1 | 3/2001 | Wen et al. | 294/1.1 |
| 6,210,754 B1 | 4/2001 | Lu et al. | 427/248.1 |
| 6,212,072 B1 | 4/2001 | Boutin et al. | 361/704 |
| 6,232,615 B1 | 5/2001 | Van Empel | 250/548 |
| 6,244,121 B1 | 6/2001 | Hunter | 73/865.9 |
| 6,275,742 B1 | 8/2001 | Sagues et al. | 700/213 |
| 6,300,974 B1 | 10/2001 | Viala et al. | 348/61 |
| 6,317,972 B1 | 11/2001 | Asai | |
| 6,323,952 B1 | 11/2001 | Yomoto | |
| 6,325,356 B1 | 12/2001 | Rozenblatt | 374/161 |
| 6,325,536 B1 | 12/2001 | Renken et al. | 374/161 |
| 6,326,228 B1 | 12/2001 | Hughes et al. | 438/49 |
| 6,373,271 B1 | 4/2002 | Miller et al. | 324/760 |
| 6,389,158 B1 | 5/2002 | Pettersen et al. | 382/154 |
| 6,422,084 B1 | 7/2002 | Fernald et al. | 73/705 |
| 6,465,281 B1 | 10/2002 | Xu et al. | |
| 6,466,325 B1 | 10/2002 | Gooch | 356/620 |
| 6,468,816 B2 | 10/2002 | Hunter | 438/14 |
| 6,476,825 B1 | 11/2002 | Croy et al. | 715/716 |
| 6,480,537 B1 | 11/2002 | Agrawal et al. | 375/240 |
| 6,518,775 B1 | 2/2003 | Yu et al. | 324/661 |
| 6,526,668 B1 | 3/2003 | Beckhart et al. | 33/366.11 |
| 6,532,403 B2 | 3/2003 | Beckhart et al. | 700/254 |
| 6,535,650 B1 | 3/2003 | Poulo et al. | 382/284 |
| D478,494 S | 8/2003 | Arnold | |
| 6,603,117 B2 | 8/2003 | Corrado et al. | 250/239 |
| 6,607,951 B2 | 8/2003 | Chen et al. | 438/199 |
| 6,614,215 B1 * | 9/2003 | Wood | 324/76.36 |
| 6,625,305 B1 | 9/2003 | Keren | 382/162 |
| 6,628,803 B1 | 9/2003 | Wakashiro et al. | 382/103 |
| 6,681,151 B1 | 1/2004 | Weinzimmer et al. | 700/259 |
| 6,691,068 B1 | 2/2004 | Freed et al. | 702/187 |
| 6,700,391 B2 | 3/2004 | Strack et al. | 324/662 |
| 6,724,930 B1 | 4/2004 | Kosaka et al. | 382/154 |
| D490,276 S | 5/2004 | Pereira et al. | |
| 6,734,027 B2 | 5/2004 | Jonkers | 438/14 |
| 6,768,545 B2 | 7/2004 | Matsuda et al. | 356/338 |
| 6,801,257 B2 | 10/2004 | Segev et al. | 348/296 |
| 6,807,503 B2 | 10/2004 | Ye et al. | 702/117 |
| 6,816,755 B2 | 11/2004 | Habibi et al. | 700/259 |
| 6,836,212 B2 | 12/2004 | Sawinski | 340/539.23 |
| 6,852,975 B2 | 2/2005 | Riegl et al. | 250/334 |
| 6,852,988 B2 | 2/2005 | Li | 700/302 |
| 6,891,276 B1 | 5/2005 | Chiang | |
| 6,898,558 B2 | 5/2005 | Klekotka | 702/188 |
| 6,925,356 B2 | 8/2005 | Schauer et al. | 700/213 |
| 6,956,230 B1 | 10/2005 | Gharib et al. | |
| 6,958,768 B1 | 10/2005 | Rao et al. | 348/86 |
| 6,966,235 B1 * | 11/2005 | Paton | 73/865.9 |
| 6,985,169 B1 | 1/2006 | Deng et al. | 648/61 |
| 6,990,215 B1 | 1/2006 | Brown et al. | 382/106 |
| 7,000,454 B2 | 2/2006 | Schneider et al. | 73/31.03 |
| 7,002,682 B2 | 2/2006 | Girvin et al. | 356/335 |
| 7,031,560 B2 | 4/2006 | Lelong-Feneyrou et al. | 385/12 |
| 7,035,913 B2 | 4/2006 | Culp et al. | 709/218 |
| 7,059,936 B2 | 6/2006 | Prasad | |
| 7,135,852 B2 | 11/2006 | Renken et al. | 324/158.1 |
| 7,149,643 B2 | 12/2006 | Renken et al. | 702/122 |
| 7,151,366 B2 | 12/2006 | Renken et al. | 324/158.1 |
| 7,158,857 B2 | 1/2007 | Schauer et al. | 700/218 |
| 7,180,607 B2 | 2/2007 | Kyle et al. | 356/614 |
| 7,206,080 B2 | 4/2007 | Kochi et al. | 356/611 |
| 7,222,789 B2 | 5/2007 | Longacre et al. | 235/450 |
| 7,283,255 B2 | 10/2007 | Ramsey et al. | 356/620 |
| 7,289,230 B2 | 10/2007 | Ramsey et al. | 356/622 |
| 7,355,706 B2 | 4/2008 | Girvin et al. | 356/338 |
| 7,360,463 B2 * | 4/2008 | Renken | 73/866.1 |
| 7,456,977 B2 | 11/2008 | Ramsey et al. | 356/620 |
| 7,502,110 B2 | 3/2009 | Saunders et al. | 356/336 |
| 7,616,126 B2 * | 11/2009 | Kadwell et al. | 340/630 |
| 7,757,574 B2 * | 7/2010 | Renken et al. | 73/866.1 |
| 7,819,033 B2 * | 10/2010 | Renken | 73/866.1 |
| 7,993,525 B2 * | 8/2011 | Su et al. | 210/695 |
| 8,033,190 B2 * | 10/2011 | Renken et al. | 73/866.1 |
| 8,105,848 B2 * | 1/2012 | Su et al. | 436/526 |
| 2001/0034222 A1 | 10/2001 | Roustaei et al. | 455/403 |
| 2001/0050769 A1 | 12/2001 | Fujinaka | 356/121 |
| 2002/0006675 A1 | 1/2002 | Shigaraki | 438/4 |
| 2002/0006687 A1 | 1/2002 | Lam | |
| 2002/0016068 A1 | 2/2002 | Nakano et al. | |
| 2002/0028629 A1 | 3/2002 | Moore | 451/6 |
| 2002/0078770 A1 | 6/2002 | Hunter | 73/865.9 |
| 2002/0092369 A1 | 7/2002 | Hunter | 73/865.9 |
| 2002/0101508 A1 | 8/2002 | Pollack | 348/85 |
| 2002/0148307 A1 | 10/2002 | Jonkers | 73/865.9 |
| 2003/0001083 A1 | 1/2003 | Corrado et al. | 250/239 |
| 2003/0112448 A1 | 6/2003 | Maidhof et al. | 356/603 |
| 2003/0127589 A1 | 7/2003 | Corrado et al. | 250/239 |

(56) References Cited

U.S. PATENT DOCUMENTS

| | | | |
|---|---|---|---|
| 2003/0133372 A1 | 7/2003 | Fasen et al. | 369/43 |
| 2003/0160883 A1 | 8/2003 | Ariel et al. | 348/308 |
| 2003/0209097 A1 | 11/2003 | Hunter | 73/865.9 |
| 2003/0223057 A1 | 12/2003 | Ramsey et al. | 356/147 |
| 2004/0158426 A1 | 8/2004 | Gershenzon et al. | |
| 2004/0202362 A1 | 10/2004 | Ishikawa et al. | 382/153 |
| 2004/0231409 A1 | 11/2004 | Lelong-Feneyrou et al. | 73/152.51 |
| 2005/0017712 A1 | 1/2005 | Le | |
| 2005/0086024 A1 | 4/2005 | Seeberger, Jr. et al. | 702/150 |
| 2005/0139542 A1 | 6/2005 | Dickensheets et al. | 210/490 |
| 2005/0224899 A1 | 10/2005 | Ramsey et al. | 257/414 |
| 2005/0224902 A1 | 10/2005 | Ramsey et al. | 257/433 |
| 2005/0233770 A1 | 10/2005 | Ramsey et al. | 455/561 |
| 2006/0000411 A1 | 1/2006 | Seo et al. | 118/715 |
| 2006/0000964 A1 | 1/2006 | Ye et al. | |
| 2006/0001874 A1 | 1/2006 | Matsuda et al. | 356/338 |
| 2006/0005632 A1 | 1/2006 | Chen et al. | 73/780 |
| 2006/0017926 A1 | 1/2006 | Pochy et al. | 356/338 |
| 2006/0055415 A1 | 3/2006 | Takita | 324/658 |
| 2006/0118518 A1 | 6/2006 | Rusu et al. | 216/67 |
| 2006/0151606 A1 | 7/2006 | Ramsey et al. | 235/454 |
| 2006/0171561 A1 | 8/2006 | Ramsey et al. | 382/103 |
| 2006/0185432 A1 | 8/2006 | Weinberg | 73/510 |
| 2006/0222480 A1 | 10/2006 | Duhamel et al. | 414/744.8 |
| 2006/0289296 A1 | 12/2006 | Maruyama et al. | 204/192.32 |
| 2007/0044579 A1* | 3/2007 | Yamaguchi et al. | 73/865.5 |
| 2007/0194908 A1* | 8/2007 | Ayala | 340/521 |
| 2007/0222462 A1 | 9/2007 | Gardner et al. | 324/662 |
| 2008/0018485 A1* | 1/2008 | Kadwell et al. | 340/630 |
| 2008/0038810 A1* | 2/2008 | Pollack et al. | 435/283.1 |
| 2008/0087116 A1 | 4/2008 | Rate et al. | 73/865.9 |
| 2008/0160639 A1* | 7/2008 | Su et al. | 436/526 |
| 2008/0228430 A1 | 9/2008 | Bonciolini | |
| 2008/0231291 A1 | 9/2008 | Ramsey et al. | |
| 2008/0246493 A1 | 10/2008 | Gardner et al. | |
| 2009/0015268 A1 | 1/2009 | Gardner et al. | |
| 2009/0117555 A1* | 5/2009 | Kuypers et al. | 435/6 |

FOREIGN PATENT DOCUMENTS

| | | | | |
|---|---|---|---|---|
| DE | 10105774 A1 | 8/2001 | | G01S 17/89 |
| EP | 0583007 B1 | 10/1997 | | |
| EP | 05830071 B1 | 10/1997 | | |
| EP | 1150187 A2 | 10/2001 | | |
| EP | 1184805 A1 | 3/2002 | | |
| EP | 1 253 471 | 10/2002 | | |
| GB | 2335737 | 9/1999 | | |
| JP | 57 120842 | 7/1982 | | |
| JP | 01082823 | 9/1987 | | |
| JP | 62054108 | 9/1987 | | |
| JP | 62220833 | 9/1987 | | |
| JP | 01223334 | 9/1989 | | |
| JP | 3108635 | 5/1991 | | |
| JP | 3214783 A2 | 9/1991 | | |
| JP | 06163340 | 11/1992 | | |
| JP | 06076193 | 6/1993 | | |
| JP | 7074229 | 6/1993 | | |
| JP | 163340 | 6/1994 | | |
| JP | 7280644 A2 | 10/1995 | | |
| JP | 8233855 A2 | 9/1996 | | |
| JP | 11307606 | 4/1998 | | |
| JP | 11260706 | 9/1999 | | 21/27 |
| JP | 328554 | 11/1999 | | |
| JP | 2000019095 | 1/2000 | | |
| JP | 2002357532 | 12/2002 | | |
| JP | 2004276151 | 10/2004 | | |
| JP | 2006214744 | 8/2006 | | |
| WO | WO 00/12263 | 3/2000 | | |
| WO | WO 00/70495 | 11/2000 | | |
| WO | WO0165317 A2 | 9/2001 | | |
| WO | WO 0167831 | 9/2001 | | |
| WO | WO 01/88976 | 11/2001 | | |
| WO | WO 02/17364 | 2/2002 | | |
| WO | WO 02/29385 | 4/2002 | | |
| WO | WO 02/47115 | 6/2002 | | |
| WO | WO 02/17364 | 11/2002 | | |
| WO | WO 03/060989 A1 | 7/2003 | | |

OTHER PUBLICATIONS

NSF Award Abstract—#9628420, https://www.fastlane.nsf.gov/servlet/showaward?award=9628420.

Notification of Transmittal of the International Preliminary Report from International Application No. PCT/US05/007423, filed Mar. 9, 2005; Notification of Transmittal of the International Search Report and Written Opinion from International Application No. PCT/US05/007423, filed Mar. 9, 2005.

Notification of Transmittal of the International Search Report and Written Opinion from International Application No. PCT/US05/007656, filed Mar. 9, 2005; Notification of Transmittal of the International Preliminary Report on Patentability from Intenational Application No. PCT/US05/007656, filed Mar. 9, 2005.

Notification of Transmittal of International Preliminary Examination Report from International Application No. PCT/US05/007418, filed Mar. 9, 2005; Notification of International Search Report and Written Opinion from International Application No. PCT/US05/007418, filed Mar. 9, 2005.

Second Office Action for Chinese patent application No. 200780036092.7 dated Aug. 30, 2010.

Notification of Transmittal of the International Preliminary Report from International application No. PCT/US2007/020814, dated May 20, 2008; Notification of Transmittal of the International Search Report and Written Opinion from International application No. PCT/US2007/020814.

Notification of Transmittal of the International Preliminary Report from International application No. PCT/US07/004350, dated Feb. 28, 2008.

Notification of Transmittal of the International Preliminary Report from International application No. PCT/US07/004350, dated Nov. 14, 2007.

Office Action of the Chinese Patent Office in foreign application No. 200580007352.9 filed Mar. 9, 2005.

Office Action of the Chinese Patent Office in foreign application No. 200580007349.7 filed Mar. 9, 2005.

Office Action of the Chinese Patent Office in foreign application No. 200580007354.8 filed Mar. 9, 2005.

Notification of Transmittal of the International Preliminary Examination Report from International application No. PCT/US05/007418, filed Mar. 9, 2005; Notification of Transmittal of the International Search Report and Written Opinion from International application No. PCT/US05/007418, filed Mar. 9, 2005.

Notification of Transmittal of the International Preliminary Examination Report from International application No. PCT/US05/007423, filed Mar. 9, 2005; Notification of Transmittal of the International Search Report and Written Opinion from International application No. PCT/US05/007423, filed Mar. 9, 2005.

International Preliminary Examination Report and Written Opinion from International application No. PCT/US05/007656, filed Mar. 9, 2005; Notification of Transmittal of the International Search Report and Written Opinion from International application No. PCT/US05/007656, filed Mar. 9, 2005.

International Search Report and Written Opinion for application No. PCT/US2008/008452, dated Nov. 6, 2008.

The First Office Action for Chinese Patent application No. 200780006216.7 dated May 12, 2010.

Second Office Action of the Chinese Patent Office in foreign application No. 200580007352.9 filed Mar. 9, 2005.

Second Office Action of the Chinese Patent Office in foreign application No. 200580007349.7 filed Mar. 9, 2005.

Second Office Action of the Chinese Patent Office in foreign application No. 200580007354.8 filed Mar. 9, 2005.

Notification of Transmittal of International Preliminary Examination Report from International Application No. PCT/US03/003247, filed Feb. 4, 2003; International Search Report and Written Opinion from International Application No. PCT/US03/003247, filed Feb. 4, 2003.

(56) References Cited

OTHER PUBLICATIONS

First Office Action issued for Chinese patent application No. 200780036092.7, dated Jan. 8, 2010.
First Office Action for the corresponding Japanese patent application No. 2009530410 dated Jun. 12, 2012.
Official Action from counterpart Korean patent application No. 10-2009-7002270, dated Sep. 23, 2013. 7 pages.
"Final Report on Wireless Wafer Proof-of-Principle," J.B. Wilgen, et al., Oak Ridge National Laboratory, Jan. 18, 1998.
"Autonomous Micro-sensor Arrays for Process Control of Semiconductor Manufacturing Processes," Darin Fisher, et al., Jun. 4, 1998. NSF Award Abstract—#49628420, https://www.fastlane.nsf.gov/servlet/showaward?award=9628420; Sep. 12, 2002.
Invitation to Pay Fees from international Application No. PCT/US2005/007656, filed Mar. 3, 2005.
International Preliminary Examination Report from International Application No. PCT/US03/03247, filed Feb. 4, 2003.
Notification of Transmittal of the International Preliminary Report from International Application No. PCT/US05/007423, filed Mar. 9, 2005; Copy of Notification of Transmittal of the International Search Report and Written Opinion from International Application No. PCT/US05/007423, filed Mar. 9, 2005.
Notification of Transmittal of the International Search Report from International Application No. PCT/US05/007656, filed Mar. 9, 2005, Copy of Notification of Transmittal of the International Preliminary Report on Patentability from Intenational Application No. PCT/US05/007418, filed 9, 2005.
Notification of Transmittal of International Preliminary Examination Report from International Application No. PCT/US05/007418, filed Mar. 9, 2005; Copy of Notification of International Search Report and Written Opinion from International Application No. PCT/US05/007418, filed Mar. 9, 2005.
International Preliminary Report on Patentability for Patent Application PCT/US2007/020814, filed Sep. 27, 2007.
Written Opinion from International Application No. PCT/US03/03247, filed Feb. 4, 2003.
Search Report from International Application No. PCT/US03/03247, filed Feb. 4, 2003.
Invitation to Pay Fees from International Application No. PCT/US03/03247, filed Mar. 3, 2005.

* cited by examiner

SUBSTRATE-LIKE PARTICLE SENSOR

CROSS-REFERENCE TO RELATED APPLICATION

The present application is based on and claims the benefit of U.S. provisional patent application Ser. No. 60/848,336, filed Sep. 29, 2006, the content of which is hereby incorporated by reference in its entirety.

BACKGROUND

The leading edge of the semiconductor processing industry is currently advancing production to the 65 nanometer and 45 nanometer nodes. Further, development is currently underway at the 32 nanometer and 22 nanometer nodes. Accordingly, it is increasingly critical that semiconductor processing tools and the processing itself be controlled to tolerances and conditions never previously required. The cost of wafer scrap and maintenance downtime continues to drive the desire to control processes and equipment to tighter levels, and as other problems arise that were insignificant to processes above 100 nanometers, process and equipment engineers look for new and innovative ways to better control semiconductor processing.

During the manufacture of semiconductor wafers, there are multiple tools and process steps to which a wafer is exposed. During each of these steps there are potential defects that may be caused by dirty equipment and/or poor process conditions that can cause degradation in yield of the final integrated circuit devices due to microscopic particles being deposited on the wafer's surface. Thus, it is critical to keep all process stages and steps as clean as reasonably possible and to be able to monitor the condition of these various stages before committing wafers to the process. This is important because each wafer may contain the circuitry for tens or even hundreds of integrated circuit devices, and a single lost wafer may result in hundreds or thousands of dollars worth of scrap.

Traditionally, wafers are test-run through the semiconductor processing tool and particles on the wafer are counted both before and after the test run. The difference in the number of particles is then attributed to the tool. This is a time-consuming process and may not provide any indication of where, within the tool, the particles were deposited. Accordingly, if too many particles are found on a given test run wafer, it simply indicates that the semiconductor processing tool is too dirty and that further technician efforts are required to open the tool, identify the source(s) of particles, and generate appropriate corrective action. Once this process is complete, the wafer must be test run again and the entire process repeated until there is simply an indication that the semiconductor processing tool is suitably clean.

SUMMARY

A substrate-like particle sensor includes a substrate-like base portion and an electronics enclosure disposed on the substrate-like base portion. A power source is located within the electronics enclosure. A controller is operably coupled to the power source. A particle sensor is operably coupled to the controller and provides an indication to the controller of at least one particle present near the particle sensor.

DETAILED DESCRIPTION

Embodiments of the present invention generally provide real-time sensing of particles present within the sealed environment of a semiconductor processing tool. The sensing of particles can be done in accordance with various techniques. One exemplary technique provided herein includes optically sensing particles proximate a substrate-like wireless sensor. Another embodiment includes sensing the mass of particles deposited upon a mechanical structure coupled to the wireless substrate-like sensor.

Figure 1:
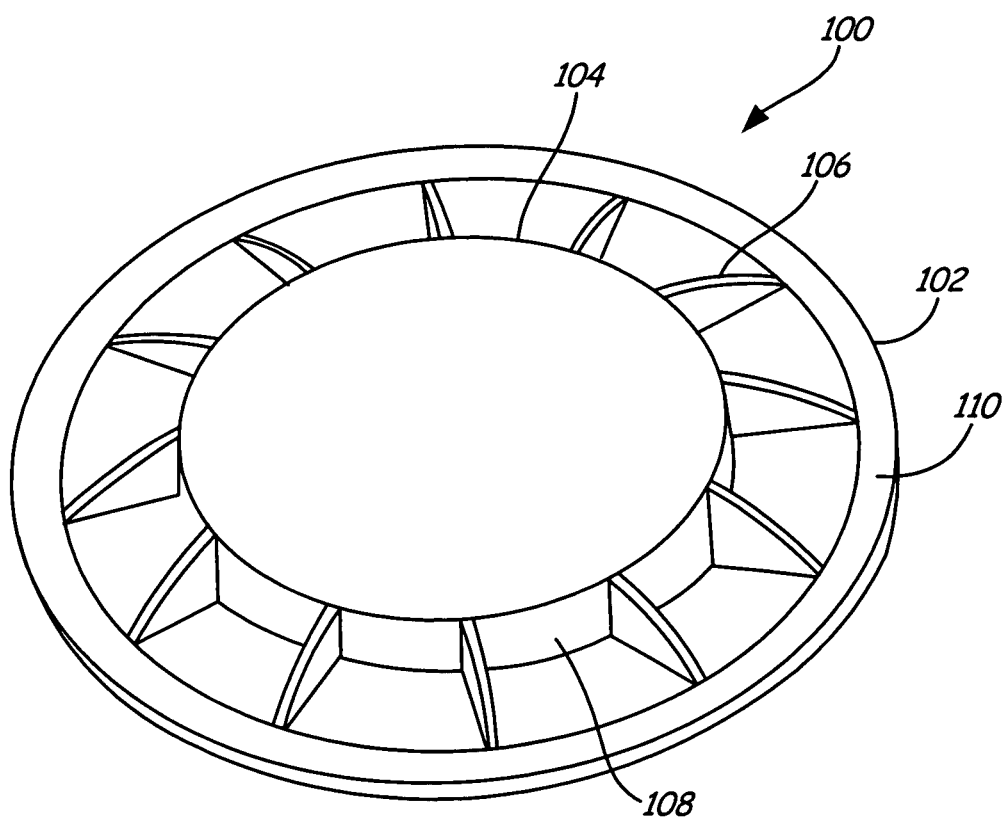
FIG. 1 is a perspective view of a wireless substrate-like sensor with which embodiments of the present invention are particularly useful.

FIG. 1 is a perspective view of a wireless substrate-like sensor with which embodiments of the present invention are particularly useful. Sensor 100 includes substrate-like portion 102 that is preferably sized to have a diameter that is equal to that of a standard substrate size. Exemplary sizes include a 200 millimeter diameter, or a 300 millimeter diameter. However, as different standards are developed or employed, this dimension can vary. Sensor 100 includes electronics housing or enclosure 104 that is disposed upon substrate-like portion 102. In order to increase rigidity of the overall sensor 100, a plurality of fins or struts 106 are provided that couple side wall 108 of electronics enclosure 104 to surface 110 of substrate-like portion 102. In order to pass easily through the sealed semiconductor processing chamber, it is desirable for substrate-like sensor 102 to have a form factor that is very similar, if not identical, to an actual substrate. Common wafer dimensions and characteristics may found in the following specification: SEMI M1-0302, "Specification for Polished Monochrystoline Silicon Wafers", Semiconductor Equipment and Materials International, www.semi.org.

Figure 2:
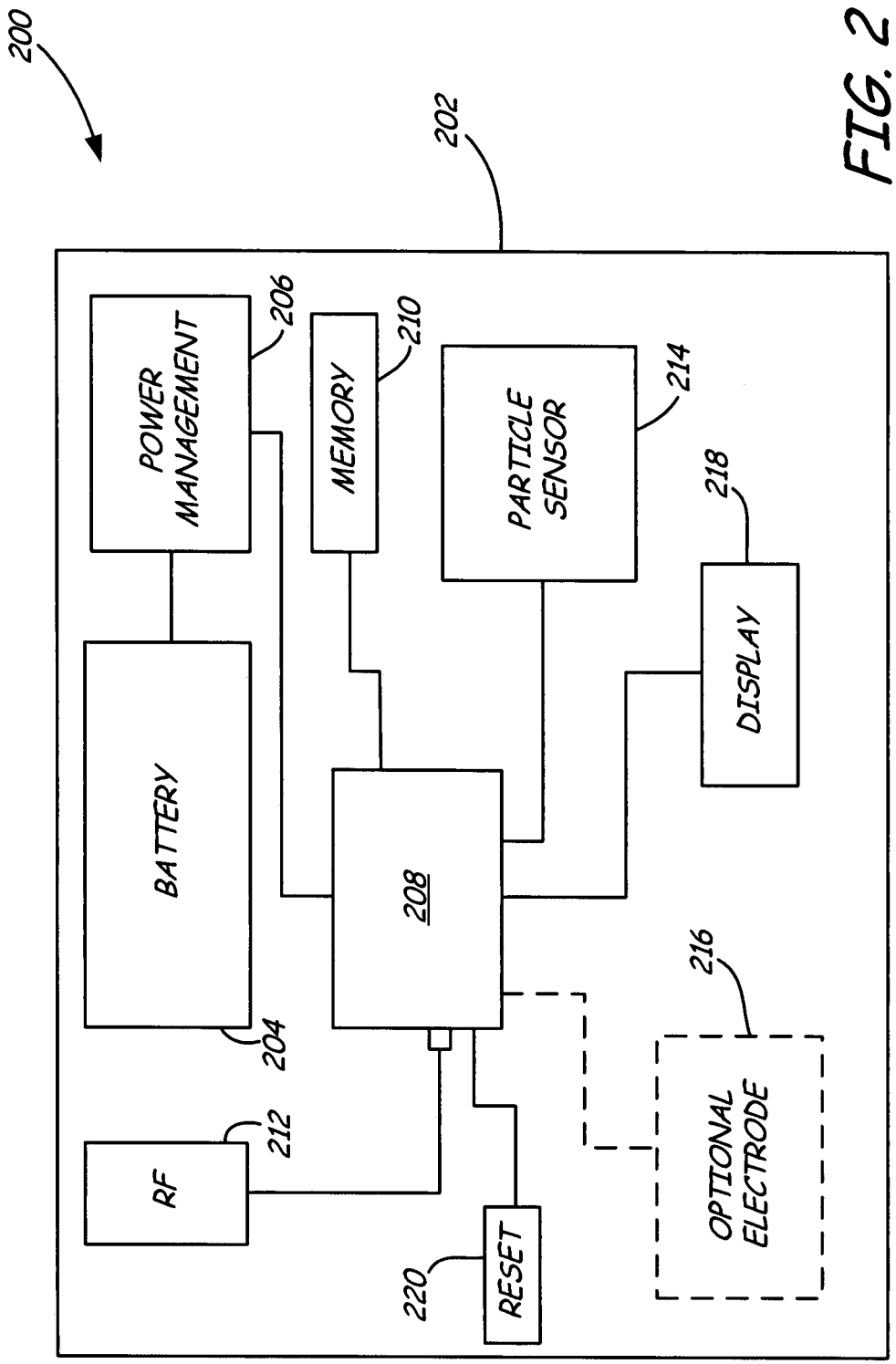
FIG. 2 is a block diagram of a wireless substrate-like particle sensor in accordance with an embodiment of the present invention.

FIG. 2 is a block diagram of a wireless substrate-like particle sensor in accordance with an embodiment of the present invention. Sensor 200 includes electronics enclosure 202, which may be identical to enclosure 104. Disposed within enclosure 202 are power source 204, power management module 206, and controller 208. Additionally, memory 210 is also disposed within enclosure 202 and is coupled to controller 208. Further still, radio frequency module 212 is disposed within enclosure 202 and coupled to controller 208.

While particle sensor 214 is illustrated in FIG. 2 as being disposed within enclosure 202, it may form part of enclosure 202, or may be disposed proximate, but external to enclosure 202.

As illustrated in FIG. 2, power source 204 is preferably a battery disposed within enclosure 202 and is coupled to controller 208 via power management module 206. Preferably, power management module 206 is a power management integrated circuit available from Linear Technology Corporation under the trade designation LTC3443. Controller 208 is preferably a microprocessor available from Texas Instruments under the trade designation MSC1211Y5. Controller 208 is coupled to memory module 210, which can take the form of any type of memory, including memory that is internal to controller 208 as well as memory that is external to controller 208. The preferred controller includes internal SRAM, flash RAM and boot ROM. Memory module 210 also preferably includes external flash memory having a size of 64K×8. Flash memory is useful for storing such non-volatile data as programs, calibration data, and/or non-changing data as may be required. The internal random access memory is useful for storing volatile data relevant to program operation.

Controller 208 is coupled via a suitable port, such as a serial port, to radio frequency communication module 212 in order to communicate with external devices. In one embodiment, radio-frequency module 212 operates in accordance with the well-known Bluetooth standard, Bluetooth core specification version 1.1 (Feb. 22, 2001), available from the Bluetooth SIG (www.bluethooth.com). One example of module 212 is available form Mitsumi under the trade designation WMLC40. Additionally, other forms of wireless communication can be used in addition to, or instead of, module 212. Suitable examples of such wireless communication include any other form of radio frequency communication, acoustic communication, infrared communication or even communication employing magnetic induction.

Controller 208 is coupled to particle sensor 214 which is configured to sense one or more particles proximate sensor 200 within the sealed environment of a semiconductor processing tool. Sensor 214 can preferably sense not only particle presence (in order to generate particle counts), but can also sense a characteristic of individual particles, such as mass and/or size. While an embodiment described below specifically addresses particle mass, particle size can be sensed by using a multi-pixel image sensor, such as a line sensor, or array, and detecting how many pixels sense the shadow of a particle.

Sensor 200 can also include optional electrode 216 which preferably forms an electrostatic plate that is disposed to attract particles floating in the air proximate sensor 200 to particle sensor 214 to be sensed more efficiently. The details of the way in which optional electrode 216 performs this function will be described with respect to distinct embodiments described below.

Sensor 200 preferably includes a display 218 that is configured to provide a particle count and/or display a go/no go indication to the process engineer. Additionally, in order to reset the particle count, reset button 220 is also provided and is coupled to controller 208.

Figure 3:
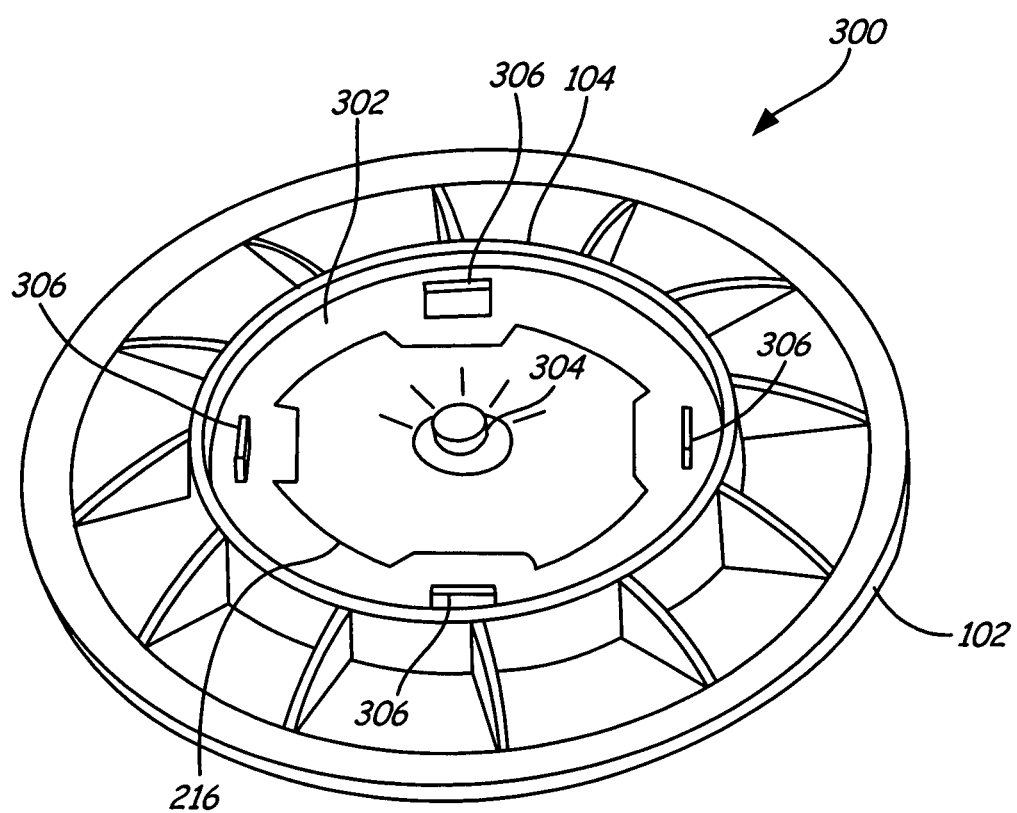
FIG. 3 is a perspective view of a wireless substrate-like particle sensor 300 in accordance with an embodiment of the present invention.

FIG. 3 is a perspective view of a wireless substrate-like particle sensor 300 in accordance with an embodiment of the present invention. Sensor 300 bears many similarities to sensors 100 and 200, and like components are numbered similarly. Sensor 300 has an electronics enclosure 104 with a recessed surface 302. Within electronics enclosure 104 below surface 302, all of the electronics, such as those illustrated in FIG. 2, are disposed. The embodiment illustrated in FIG. 3 provides an optical technique for measuring particles proximate sensor 300. Specifically, particle sensor 214 includes light source 304 disposed near the center of surface 302. Light source 304 may be an LED, a laser, or any other suitable light source. At least one illumination sensor 306 is disposed near a periphery of surface 302. Further, it is preferred that a number of mirrors (shown in FIG. 4) be included near the periphery of surface 302. Illumination emanating from source 304 essentially travels out in all directions, and, when no particles are present, generates substantially constant illumination signals at each of sensors 306. When one or more particles enters the area between source 304 and one of detectors 306, that detector 306 will note a fluctuation in the light intensity. This fluctuation can increment the particle count, or be stored in some other suitable fashion. While FIG. 3 illustrates source 304 as generating illumination in substantially all directions, it is expressly contemplated that source 304 may generate one or more directional beams, whether comprised of structured illumination or not, that may interact with one or more mirrors before finally impinging upon a detector 306. In this way, more of the area proximate surface 302 can be monitored for interactions with particles.

FIG. 3 also illustrates optional electrode 216 in the form of a relatively large plate. Electrode 216 is preferably an electrostatic electrode that is maintained, in known fashion, at a potential that will attract particles.

While the embodiment illustrated with respect to FIG. 3 illustrates one or more beams or rays of illumination moving from a static source to a plurality of static sensors, it is also expressly contemplated that one or more beams could be scanned, or otherwise passed proximate surface 302, for example by using moving mirrors. Further still, in either the embodiment shown in FIG. 3, or the scanning beam embodiment, the beam or illumination may be collimated vertically, but diverging horizontally so that the angular coverage is enhanced without their physical scanning.

Figure 4:
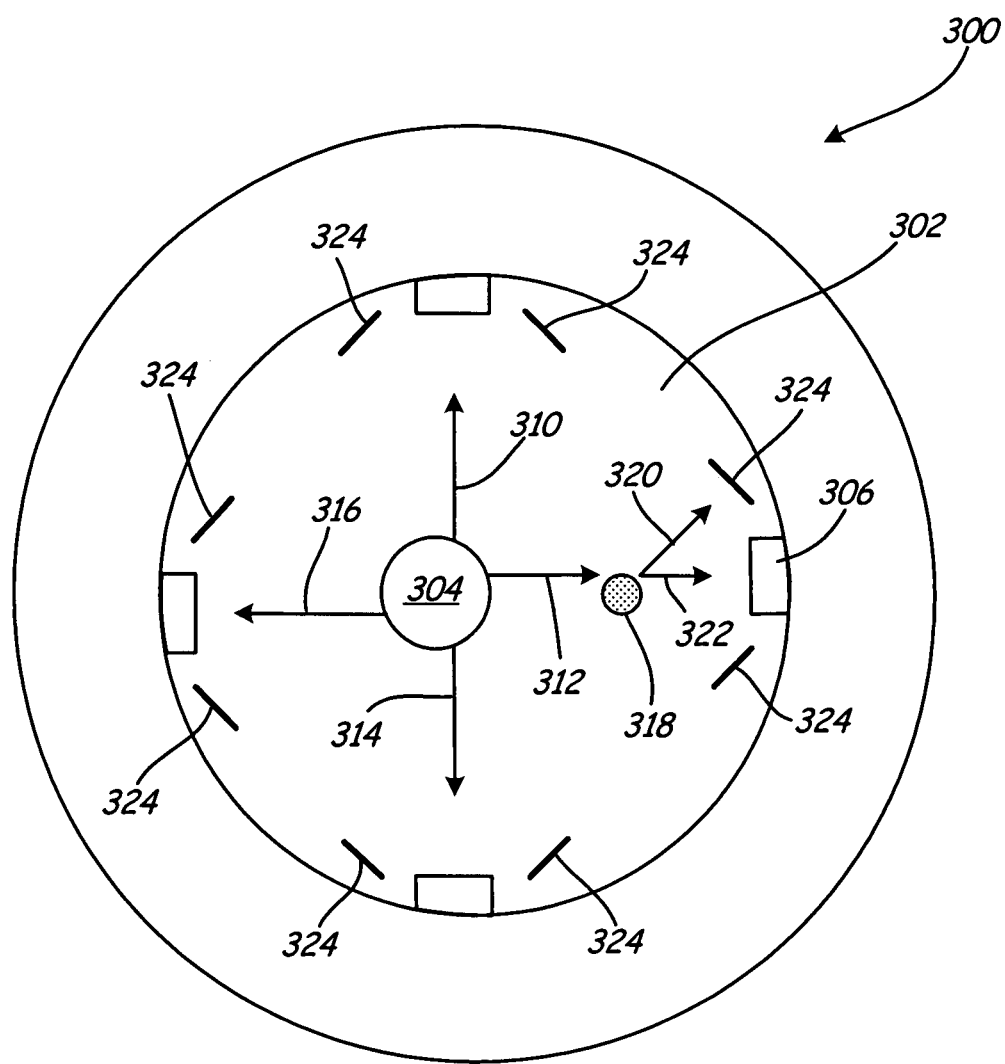
FIG. 4 is a top plan view illustrating a sensor in accordance with an embodiment of the present invention.

FIG. 4 is a top plan view illustrating sensor 300 in accordance with an embodiment of the present invention. Source 304 generates illumination in directions 310, 312, 314 and 316. Illumination 312 is illustrated impinging a particle 318, which is shown with a grossly exaggerated size. A portion of the illumination is then deflected as illustrated at line 320, and only illumination 322 reaches detector 306. Detector 306 senses this momentary change in illumination intensity, and registers a particle to controller 208. FIG. 4 also illustrates a number of mirrors 324 that help facilitate or otherwise generate larger optical paths along the plane proximate and substantially parallel to surface 302.

While the illumination described with respect to the embodiments illustrated in FIGS. 3 and 4 can take any suitable form, it is preferred that the illumination have a relatively short wavelength, such as in the blue, or even ultraviolet spectral range, since longer wavelength illumination will be less scattered by the very small particles. Accordingly, short wavelength illumination is preferable since process technology is advancing to smaller and smaller critical dimensions. Further, while the optical-based embodiment described with respect to FIGS. 3 and 4 generally measure light emanating from a central source, one or more sensors can be used or arranged such that they do not normally see light from the centralized source, but instead see light from scattered particle interactions. Accordingly, in such embodiments, when there is no particle in the beam, there is not scattered light detected. Conversely, when there is a particle in the beam, scattered light is detected. Moreover, combinations of detectors detecting both non-scattered and scattered light can be used to reduce the likelihood of false particle detentions.

Figure 5:
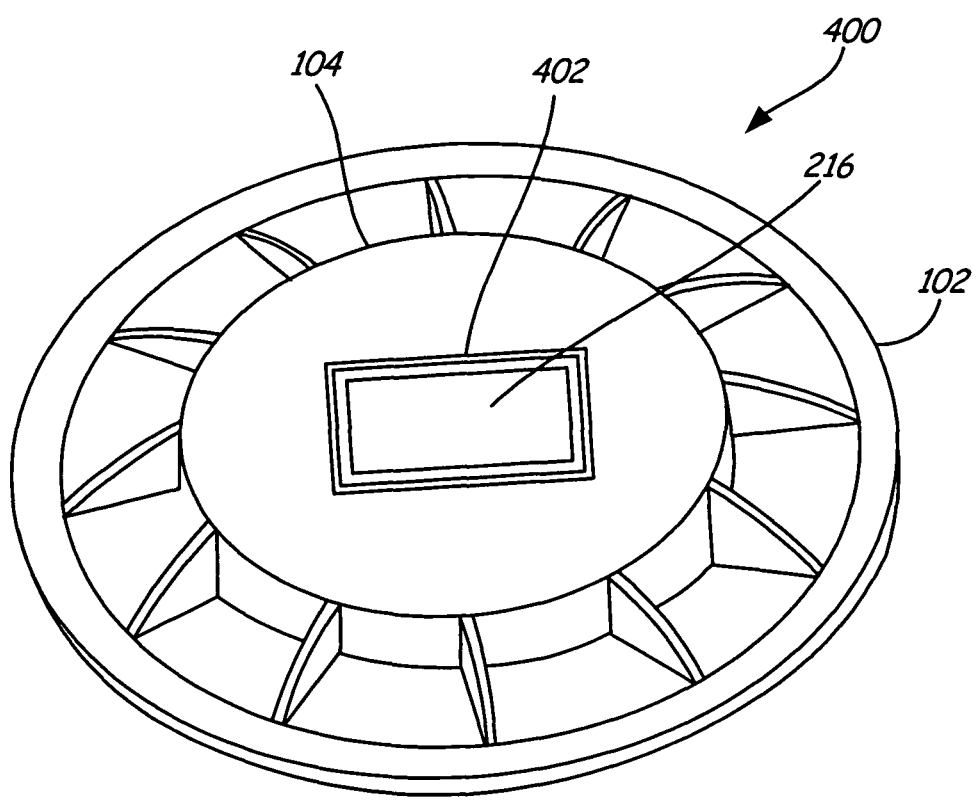
FIG. 5 is a perspective view of a wireless substrate-like particle sensor in accordance with another embodiment of the present invention.

FIG. 5 is a perspective view of a wireless substrate-like particle sensor in accordance with another embodiment of the present invention. Sensor 400 bears some similarities to sensors 100 and 300, and like components are numbered similarly. Sensor 400 differs from previously-described sensors in that sensor 400 determines particle quantity by essentially measuring the mass of particles that adhere to structure 402. Structure 402 is preferably a microelectromechanical system (MEMS) that includes a piezoelectric element that is able to excite, or otherwise drive, structure 402 in order to determine its resonant frequency. As particles adhere to structure 402, the mass of the combined particles/structure 402 will change, and accordingly change the resonant frequency. In order to enhance the efficiency of sensor 400, it is also preferred that sensor 400 include optional electrostatic electrode 216 disposed on structure 402. In this manner, particles floating proximate structure 402 will be urged, via electrostatic force, to adhere to structure 402. Structure 402 then uses the electrostatic charge from optional electrode 216 to attract particles onto its beam or onto a proof of mass of structure 402. While it is preferred that electrode 216 maintain either a positive or negative charge, it may also alternate to attract particles and potentially scavenge particles from the semiconductor processing tool.

Figure 6:
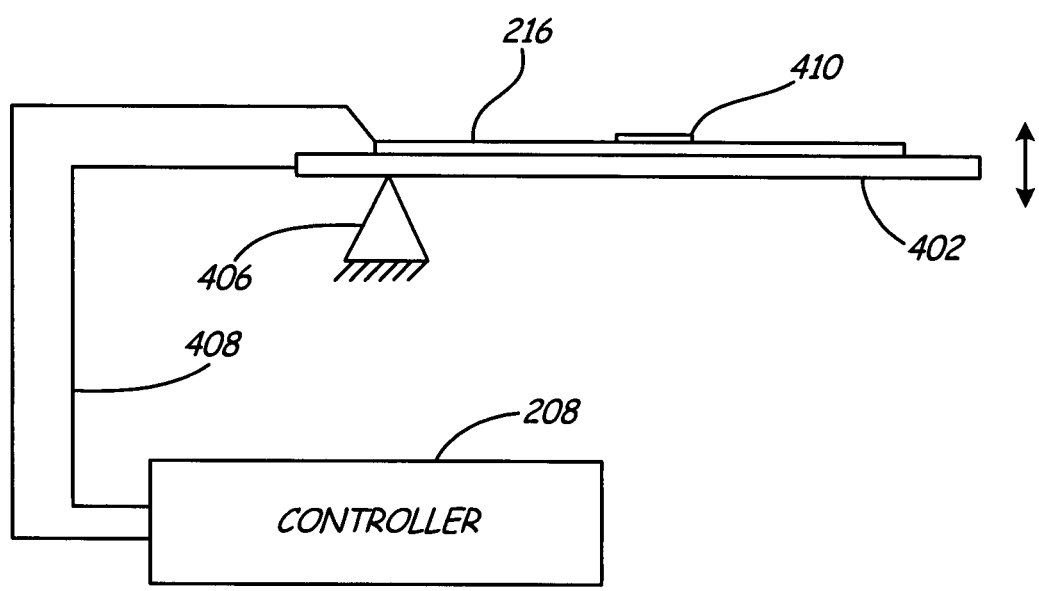
FIG. 6 is a diagrammatic view of the MEMS mass-based embodiment described with respect to FIG. 5.

FIG. 6 is a diagrammatic view of the MEMS mass-based embodiment described with respect to FIG. 5. Specifically, structure 402 is a cantilever structure in that it is supported, as illustrated diagrammatically at support 406, on or proximate one end. A portion of structure 402 is piezoelectric, or otherwise formed of a suitable microelectromechanical structure such that a current from controller 208 through line 408 generates movement within structure 402. Analyzing the electrical response of the piezoelectric element, controller 208 is able to calculate, or otherwise observe changes in, the mass of structure 402, and/or the resonant frequency of structure 402. This is because, as particles are deposited on structure 402, as indicated at reference numeral 410, the total mass and rotational inertia of the system about support 206 changes. This change is then detected as the different resonant frequency. FIG. 6 also illustrates optional electrode 216 disposed on top of structure 402 and attracting particles 410.

Embodiments of the present invention generally provide particle detection with a semiconductor processing tool that is in substantially real-time. This real-time feedback can be provided visually to a process engineer by virtue of the engineer viewing display 218 through a window in the process tool. Additionally, or alternatively, the real-time feedback can be provided via a radio frequency signal provided via radio frequency communication module 212.

Although the present invention has been described with reference to preferred embodiments, workers skilled in the art will recognize that changes may be made in form and detail without departing from the spirit and scope of the invention.

What is claimed is:

1. A substrate-like particle sensor assembly for sensing particles within a sealed processing chamber of substrates, the substrate-like particle sensor assembly comprising:
   a substrate-like base portion having a form factor that is similar to the substrates;
   an electronics enclosure disposed on the substrate-like base portion, the electronics enclosure enclosing electronics;
   a power source disposed within the electronics enclosure;
   a controller disposed within the electronics enclosure and operably coupled to the power source; and
   a particle sensor integrally attached to the electronics enclosure and operably coupled to the controller, the particle sensor having a light source disposed near a central region of the particle sensor and a plurality of illumination detectors disposed near a periphery of the particle sensor, the particle sensor also having a plurality of mirrors disposed near the periphery of the particle sensor and arranged to bend a light beam across a surface of the particle sensor.

2. The substrate-like particle sensor assembly of claim 1, wherein the light source is a laser light source.

3. The substrate-like particle sensor assembly of claim 1, wherein the light source is an LED light source.

4. The substrate-like particle sensor assembly of claim 1, and further comprising a wireless communication module that is coupled to the controller and is configured to communicate particle sensing information while the substrate-like sensor assembly is positioned within the wafer processing system.

5. The substrate-like particle sensor assembly of claim 1, wherein the controller is configured to calculate a quantity of particles present within the wafer processing system based upon a parameter sensed by the sensor.

6. The substrate-like particle sensor assembly of claim 5, and further comprising a display operably coupled to the controller and configured to provide an indication of particle quantity.

7. The substrate-like particle sensor assembly of claim 1, and further comprising a display operably coupled to the controller and configured to provide an indication of relative to particle quantity.

8. The substrate-like particle sensor assembly of claim 7, wherein the display indicates a go/no-go based upon a level of detected particles within the wafer processing system.

9. The substrate-like particle sensor assembly of claim 1, and further comprising a reset button operably coupled to the controller.

10. The substrate-like particle sensor assembly of claim 1, wherein the sensor is configured to provide an indication of particle size.

* * * * *

UNITED STATES PATENT AND TRADEMARK OFFICE
CERTIFICATE OF CORRECTION

| | | |
|---|---|---|
| PATENT NO. | : 8,823,933 B2 | Page 1 of 1 |
| APPLICATION NO. | : 11/904633 | |
| DATED | : September 2, 2014 | |
| INVENTOR(S) | : Dennis J. Bonciolini et al. | |

It is certified that error appears in the above-identified patent and that said Letters Patent is hereby corrected as shown below:

In the Claims

Column 6, Claim 7:
Line 37:

after "indication of relative" remove "to"

Signed and Sealed this
Fifth Day of April, 2016

Michelle K. Lee
*Director of the United States Patent and Trademark Office*